(12) United States Patent
Falk

(10) Patent No.: US 7,274,027 B2
(45) Date of Patent: Sep. 25, 2007

(54) SCANNING SYSTEMS AND METHODS WITH TIME DELAY SENSING

(75) Inventor: Robert A. Falk, Newcastle, WA (US)

(73) Assignee: Optometrix Inc., Renton, WA (US)

( * ) Notice: Subject to any disclaimer, the term of this patent is extended or adjusted under 35 U.S.C. 154(b) by 140 days.

(21) Appl. No.: 10/907,081

(22) Filed: Mar. 18, 2005

(65) Prior Publication Data

US 2005/0205779 A1 Sep. 22, 2005

Related U.S. Application Data

(60) Provisional application No. 60/554,496, filed on Mar. 18, 2004.

(51) Int. Cl.
*G01N 21/64* (2006.01)

(52) U.S. Cl. .................................. 250/458.1

(58) Field of Classification Search ............. 250/458.1
See application file for complete search history.

(56) References Cited

U.S. PATENT DOCUMENTS

| 6,504,167 | B2 * | 1/2003 | Ikami .......................... 250/584 |
| 6,529,271 | B1 * | 3/2003 | Engelhardt .................. 356/317 |
| 6,683,314 | B2 * | 1/2004 | Oostman et al. ......... 250/461.2 |

* cited by examiner

*Primary Examiner*—David Porta
*Assistant Examiner*—Mindy Vu
(74) *Attorney, Agent, or Firm*—Black Lowe & Graham PLLC

(57) ABSTRACT

Methods and systems that excite a test structure with an excitation beam and then sense the response of the test structure after some prescribed time interval with respect to the excitation. One or more detectors detect an emission from the test structure at a location of the test structure that is offset from a position on the test structure that is coincident with the excitation beam as the beam is scanned across the test structure.

17 Claims, 1 Drawing Sheet

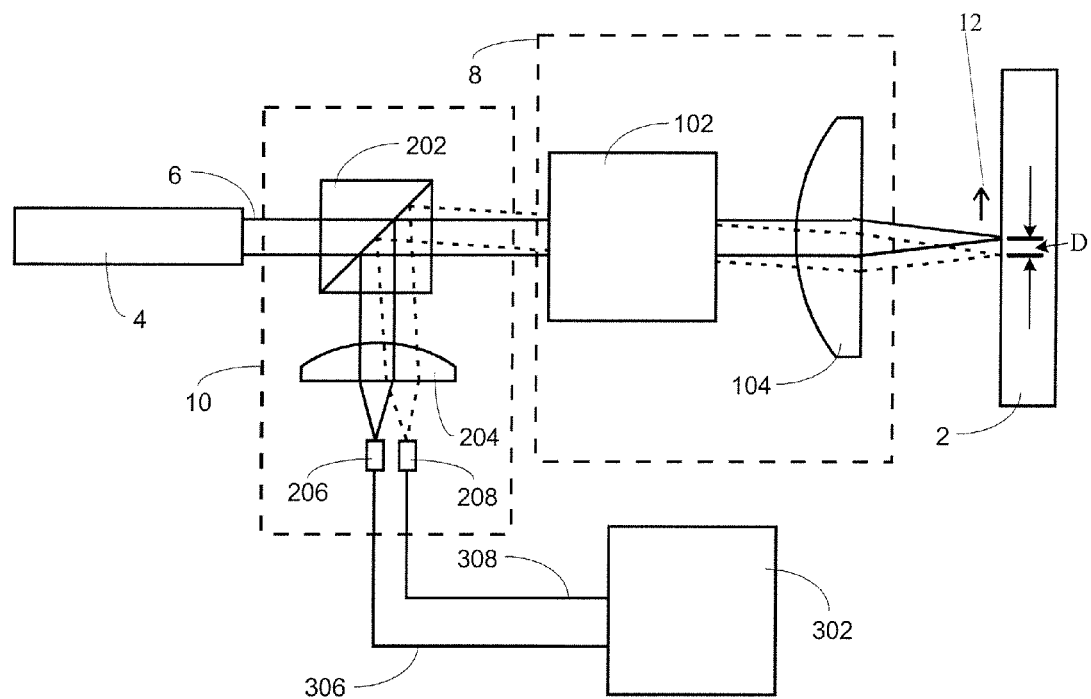

SCANNING SYSTEMS AND METHODS WITH TIME DELAY SENSING

PRIORITY CLAIM

This application claims the benefit of U.S. Provisional Application Ser. No. 60/554,496 filed Mar. 18, 2004, the contents of which are hereby incorporated by reference.

FIELD OF THE INVENTION

The present invention relates to scanning imaging systems.

BACKGROUND OF THE INVENTION

There exist several techniques in which a radiation source is used to rapidly (pulse) excite a test structure, then after a time delay the test structure is examined using a detector. Examples include:

- A pulse of light from a flash lamp is used to rapidly heat a test structure. An infrared camera rapidly records multiple images of the test structure at multiple time delays after the heating. Heat flow in the test structure can be derived from these images.
- Time resolved spectroscopy typically utilizes a pulsed laser source to excite atoms or molecules of a test structure. A fast optical detector is used to detect fluorescent decay of the excitation. Alternatively, a second fast laser pulse is used to "probe" the test structure.

It is noted in these examples that the optical detector can be both passive (e.g. a camera), or active (e.g. a laser probe). It is also noted that a multiplicity of signals collected at a multiplicity of time delays is often recorded.

In these techniques, the excitation source must be rapidly pulsed and the detection must be time delayed via electronic or other means with respect to the excitation pulse.

Therefore, there exists a need to more effectively and efficiently analyze an excited test structure.

SUMMARY OF THE INVENTION

The current invention uses the properties of a scanning system to supply an impulse of radiation to a position on a test structure and to supply a built in time delay for the detection.

Specifically, an embodiment of the present invention describes methods and systems that excite a test structure with an excitation beam and then sense the response of the test structure after some prescribed time interval with respect to the excitation.

One or more detectors detect an emission from the test structure at a location of the test structure that is offset from a position on the test structure that is coincident with the excitation beam as the beam is scanned across the test structure.

BRIEF DESCRIPTION OF THE DRAWINGS

The preferred and alternative embodiments of the present invention are described in detail below with reference to the following drawings.

FIG. 1 is a diagram illustrating an embodiment of the present invention.

DETAILED DESCRIPTION OF THE PREFERRED EMBODIMENT

FIG. 1 shows the basic components of an embodiment of the present invention as well as a specific implementation as a laser scanning or confocal microscope. The present invention senses properties of a test structure 2. The test structure 2 can be any physical object, such as an integrated circuit, a package in which the integrated circuit is housed, a printed circuit board, composite materials, etc. In one embodiment, the present invention excites and then detects a time delay response of the test structure 2.

An excitation source 4 generates an excitation beam 6 that is used to induce an excitation in the test structure 2. Examples of the excitation source 4 including but are not limited to:
 Optical, e.g. a laser
 Electron beam
 Ion beam
 Acoustic.

Each excitation source 4 can induce a range of possible excitations, including but not limited to:
 Thermal heating
 Ionization
 Photo excitation of atoms and molecules
 Photo carrier generation (e.g. in semiconductors)
 Material ablation.

The excitation beam 6 is directed towards a scanning device 8. In the case where the excitation beam 6 is an optical beam, the scanning device 8 may include a scanning mirror assembly 102 coupled with a lens 104 that focuses the excitation beam 6 onto the test structure 2. In the case where the excitation beam 6 includes an electron or ion beams, the scanning device 8 may include equivalent electromagnetic beam deflectors and focusing elements (not shown). The purpose of the scanning device 8 is to direct the excitation beam 6 on to the test structure 2 and to scan the excitation beam 6 across the test structure 2. Any assembly that produces this result is acceptable. As shown in FIG. 1, an arrow 12 indicates a possible upwards scanning motion of the excitation beam 6. In another embodiment, the test structure 2 is moved to supply the scanning function.

The excitation beam 6 produces an excitation in the test structure 2 that is moved with a velocity, V, across the surface of the test structure 2. Thus, for a specific position on the test structure 2, the excitation beam 6 appears as a pulse. A duration of the pulse is the width of the excitation beam 6 at the surface of test structure 2 divided by the velocity V. The excitation produced by this pulse can in turn produce a re-emission from the test structure 2. The re-emission can take on a variety of forms, including but not limited to:
 Thermal radiation
 Fluorescent decay
 Ablation fragments
 Electrons or ions.

The re-emission can be passive as in the above list or involve an active secondary probe as would be the case for an active laser probe for physical distortion of the test structure 2.

The re-emission is collected by the scanning device 8. The scanning device 8 sends the collected re-emission back to a detection device 10. The detection device 10 detects the re-emission of a location on the test structure 2 at some point in time after the excitation of that location on the test structure 2 occurs. Also, the detection device 10 transforms the magnitude of the re-emission into a signal that can be displayed as an image.

As the excitation beam 6 is being scanned across the test structure 2, the location on the test structure 2 that the detection device 10 detects is behind the location on the test structure 2 that is presently being excited by the excitation beam 6. As shown in FIG. 1, the detection device 10 includes one or more detectors 206 or 208. In this example, the detector 208 is positioned to collect the delayed re-emissions of the test structure 2 from a beam splitter 202. Because the detector 208 is not positioned to receive direct reflections off of the test structure 2, re-emissions are sensed by the detector 208.

The excitation beam 6 and the re-emissions detection point are scanned across the test structure 2 at a velocity V. A distance D is a distance that the re-emissions detection point is behind the position of the excitation beam, thereby causing the detection of the re-emission to take place at a time delay or time interval after the excitation takes place. The time delay or interval is the ratio of the distance over the velocity, D/V.

Both distance D and velocity V can be adjusted to allow a range of time delays. Velocity V can be adjusted using scanning controls of the scanning device 8. Distance D can be adjusted by changing position of the detector.

In another embodiment, multiple detectors may be used at various positions for simultaneously detecting re-emissions at a plurality of distances (or time delays) after excitation.

The details of FIG. 1 allow description of a specific example that may clarify the more general description. In one example, the excitation source 4 is a laser and the excitation beam 6 is a laser beam. The laser beam passes through a scanning mirror assembly (the scanning device 8), which deflects the laser beam at an angle versus time (the angle changes over time). The lens 104 transforms the angular scan into a position scan on the test structure 2.

In this example, excitation caused by the laser beam heats the surface of the test structure 2. The increased temperature that occurs will increase the amount of thermal emission that occurs. The thermal emission is the re-emission. Thermal conduction from the heated area into the cooler parts or the test structure 2 causes the thermal emission to decrease with time. A measurement of the rate of decrease in the thermal emission is a direct measurement of the thermal conduction properties of the test structure 2.

Also in this example, the beam splitter 202 allows passage of the laser beam (the excitation beam 6) while redirecting the re-emission towards a second lens 204. The second lens 204 focuses the thermal emission towards the detectors 206 or 208 that are optical detectors. The optical detectors convert the thermal emission (the re-emission) into electrical signals 306 or 308. The electrical signals 306 or 308 are converted into images that are presented on a display 302. Thus, the output of one of the optical detectors will cause a single thermal image to be displayed on the display 302.

The first detector 206 collects thermal radiation from a position coincident with the excitation beam 6. The second detector 208 collects thermal radiation from a position at a distance D behind the excitation beam 6, which is to say at a time of D/V where V is the scan velocity described above. There can be a multiplicity of detectors with a multiplicity of positions, allowing signals from a multiplicity of time delays to be collected in parallel. An equivalent apparatus could also be used to detect fluorescent decay or other types of re-emissions for the test structure 2.

While the preferred embodiment of the invention has been illustrated and described, as noted above, many changes can be made without departing from the spirit and scope of the invention. For example, because the excitation beam and emission may be any of the type described above, the lenses 104 and 204 is selected from any of number of different types of focusing devices according to the excitation beam and emission. Accordingly, the scope of the invention is not limited by the disclosure of the preferred embodiment. Instead, the invention should be determined entirely by reference to the claims that follow.

What is claimed is:

1. A time resolving imaging apparatus comprising
an excitation source for generating a excitation beam;
a scanning device for scanning the excitation beam over a test structure;
one or more detection devices for detecting an emission from the test structure, said detector devices being configured to detect an emission from the test structure at a location of the test structure that is offset from a position on the test structure that is coincident with the excitation beam, and for producing a signal related to a temporal signature based on the detected emission.

2. The apparatus of claim 1, wherein the excitation source includes a laser.

3. The apparatus of claim 1, wherein the scanning device includes a device for controlling speed of scanning the excitation beam over the test structure.

4. The apparatus of claim 3, wherein the scanning device includes a scanning mirror assembly and a lens.

5. The apparatus of claim 3, wherein the scanning device includes a scanning table for moving the test structure relative to the excitation beam.

6. The apparatus of claim 1, wherein the detection device includes a beam splitter, a lens and one or more detectors.

7. The apparatus of claim 6, wherein at least one of the one or more detectors is adjustable in position.

8. The apparatus of claim 6, wherein the one or more detectors detects emission from a portion of the test structure at a time delay after the excitation beam has excited the portion of the test structure.

9. The apparatus of claim 8, further comprising a display device coupled with the one or more detectors, the display device configured to present an image based on the detected emission.

10. The apparatus of claim 6, wherein at least one of the one or more detectors actively detects emission.

11. The apparatus of claim 6, wherein at least one of the one or more detectors passively detects emission.

12. A time resolving imaging method comprising
generating an excitation beam;
scanning the excitation beam over a test structure;
detecting one or more emissions from the test structure at a location of the test structure that is offset from a position on the test structure that is coincident with the excitation beam; and
producing a signal related to a temporal signature based on the detected one or more emissions.

13. The method of claim 12, wherein scanning includes adjusting speed of scanning the excitation beam over the test structure.

14. The method of claim 12, wherein detecting is performed by at least one detector being adjustable in position.

15. The method of claim 12, further comprising presenting an image on a display device based on the detected emission.

16. The method of claim 12, wherein detecting includes actively detecting the emission.

17. The method of claim 12, wherein detecting includes passively detecting the emission.

* * * * *